(12) United States Patent
Cullen (10) Patent No.: US 9,050,198 B2
(45) Date of Patent: Jun. 9, 2015

(54) DEVICE FOR THE ALLEVIATION OF SNORING AND SLEEP APNOEA

(76) Inventor: Stewart Cullen, Subiaco (AU)

(\*) Notice: Subject to any disclaimer, the term of this patent is extended or adjusted under 35 U.S.C. 154(b) by 890 days.

(21) Appl. No.: 12/993,697

(22) PCT Filed: May 15, 2009

(86) PCT No.: PCT/AU2009/000614
§ 371 (c)(1),
(2), (4) Date: Feb. 7, 2011

(87) PCT Pub. No.: WO2009/140720
PCT Pub. Date: Nov. 26, 2009

(65) Prior Publication Data
US 2011/0259345 A1    Oct. 27, 2011

(30) Foreign Application Priority Data
May 21, 2008 (AU) .................. 2008902516

(51) Int. Cl.
*A61F 5/56* (2006.01)
(52) U.S. Cl.
CPC ..................... *A61F 5/566* (2013.01)
(58) Field of Classification Search
CPC ....................................................... A61F 5/56
USPC ................. 128/848; 602/902; 433/140, 6
See application file for complete search history.

(56) References Cited

U.S. PATENT DOCUMENTS

| | | | |
|---|---|---|---|
| 4,671,767 A | 6/1987 | Blechman et al. | |
| 5,503,552 A | 4/1996 | Diesso | |
| 5,562,106 A | 10/1996 | Heeke et al. | |
| 5,823,193 A * | 10/1998 | Singer et al. | 128/848 |
| 6,012,920 A * | 1/2000 | Woo | 433/19 |
| 6,604,527 B1 | 8/2003 | Palmisano | |
| 6,955,172 B2 | 10/2005 | Nelson et al. | |
| 2005/0236003 A1 | 10/2005 | Meader | |
| 2008/0000483 A1 | 1/2008 | Halstrom | |
| 2008/0199824 A1 | 8/2008 | Hargadon | |
| 2010/0300458 A1* | 12/2010 | Stubbs et al. | 128/848 |

FOREIGN PATENT DOCUMENTS

WO    WO 2008/141372    11/2008

OTHER PUBLICATIONS

International Search Report from Australian Patent Office dated Aug. 26, 2009, for International Application No. PCT/AU2009/000614, 4 pages.

\* cited by examiner

*Primary Examiner* — Victoria J Hicks
(74) *Attorney, Agent, or Firm* — Edmonds & Nolte, P.C.

(57) ABSTRACT

Apparatus for the alleviation of sleep apnoea in which dentition engagement units or dental overlays shaped to engage the maxillary and mandibular dentition of a subject each having a laterally located pair of flanges the ends of which almost abut, magnets embedded in said flanges with their like poles adjacent or sinusoidally-shaped extension elements made from shape-memory material having a transition temperature equal to or slightly less than normal body temperature and accommodated in cavities in said flanges provide, respectively, a magnetic repulsion force or expansive force when warmed by body heat sufficient, during sleep-induced relaxation, to displace said mandibular dentition engagement unit or dental overlay forwardly in relation to said maxillary dentition engagement unit, displacing the mandible of the subject and thereby effecting a displacement of the temporomandibular joint.

24 Claims, 7 Drawing Sheets

DEVICE FOR THE ALLEVIATION OF SNORING AND SLEEP APNOEA

CROSS-REFERENCE TO RELATED APPLICATIONS

This application is a United States National Phase Application of International Patent Application No. PCT/AU2009/000614, filed on May 15, 2009, which claims the benefit of AU Patent Application No. 2008902516, filed on May 21, 2008, both of which are incorporated by reference herein.

This invention relates generally to devices for the alleviation of snoring and sleep apnoea and, specifically, to such devices which function by inducing mandibular advancement during sleep periods.

During sleep, it is common for airway obstruction to occur as a result of the apposition of the rear part of the tongue or soft palate with the posterior pharyngeal wall. A first result is snoring—the vibration of the oral tissues during respiration—which may be only a nuisance to a partner or perhaps result in sleep interruption. Exacerbated by obesity or loss of muscle tone in throat and oral tissues with aging, the condition may progress to obstructive sleep apnoea. This is a potentially lethal disorder in which breathing stops during sleep for 10 seconds or more for sometimes 300 times during a night of sleep. The condition has been associated with a variety of potentially serious medical conditions, such as hypertension, ischemic heart disease and stroke. It is thus desirable that diagnosis and treatment occur as early as possible.

Because of the ubiquity of the condition, a very wide variety of treatments has been proposed. These include surgery, positive ventilation methods and the use of many devices designed to provide mandibular advancement, forward displacement of the tongue or a combination of both. In the most common surgical method, uvulopalatopharyngoplasty, part of the soft palate is removed to prevent closure of the pharyngeal airway during sleep. The procedure is performed under general anaesthetic in the operating theatre. In a similar procedure, laser assisted uvulopalatoplasty, multiple treatments with laser light are employed to progressively scar and tighten the palate without removal of tissue. Therapists are now performing an improved procedure in which a single treatment with laser light is used to remove the uvula and trim the soft palate while the patient is sitting upright and fully awake. As uvulopalatopharyngoplasty may be painful and require a hospital stay of one to three days and a recuperative period of one to two weeks, it is attractive only to the most intractable sufferers. While uvulopalatoplasty is much easier to tolerate and may result in only a sore throat of one to two weeks duration and other minor effects, sufferers are still reluctant to undertake any non-reversible treatment which may have unforseen consequences. Other treatments involving the insertion of bone anchors, as taught by Sohn et al in U.S. Pat. No. 5,988,171, or the implantation of magnets in the uvula, as taught by Nelson et al in U.S. Pat. No. 6,955,172 and the like are judged generally by sufferers to be quite unattractive.

Positive ventilation methods, of which the most common is continuous positive airway pressure (CPAP), involves the use of a mask to supply pressurised air to a sleeping sufferer. The air pressure required (also called the titrated air pressure) is determined by a sleep disorders physician during an overnight study in a sleep laboratory. The titrated air pressure is usually in the range 6 to 14 centimeters of water, but extreme cases may require as high as 25 to 30 centimeters of water. While the use of CPAP usually produces an immediate improvement in sleep quality and quality of life generally, the mask and hose to the CPAP machine are ugly and cumbersome and also generally quite unattractive to many sufferers.

In relation to devices designed to effect mandibular advancement or forward displacement of the tongue, it has long been known that forward displacement of the tongue greatly reduces the tendency for its rear part to relax against the posterior pharyngeal wall, thereby alleviating snoring and, in many cases, sleep apnoea. It is also well known that advancement of the mandible carries the tongue forward in a desirable way. A mandibular advancement of up to 10 millimeters, and normally in the range of five to 10 millimeters, is required to alleviate the symptoms. While there are many devices directed specifically towards forward displacement and control of the tongue, it is the class of devices directed towards mandibular advancement that is of interest to this application.

Almost all devices directed towards mandibular advancement are based upon a pair of separate, approximately arcuate dentition engagement units. Each of these has one more or less flat face which abuts a complementary face of the other. Each has an opposed dentition engagement face which is adapted to accurately engage, as appropriate, all or part of the maxillary or mandibular dentition. The dentition engagement faces, commonly referred to as dental overlays, are moulded from dental impressions made in the normal way or created directly by a user. This latter is done by the user biting into a shaped quantity of thermoplastic or settable resin material provided on the dentition engagement units, the material then retaining an impression of the dentition during setting. The two dentition engagement units are located in correct juxtaposition while the dental impressions are made by biting. In their simplest application, the dentition engagement units are joined or hinged in a way providing the requisite degree of mandibular advancement and closing of the jaws to enter the teeth fully into the dental impressions acts to effect the advancement. Examples of this type of application are those taught by Heeke et al in U.S. Pat. No. 5,562,106 and Lampert in U.S. Pat. No. 6,767,207. In another application, typified by those taught by Belfer in U.S. Pat. Nos. 5,720,302, 5,810,013 and 5,921,241, tension is simply maintained on a lower dentition engagement unit through an extension member connected to an oral shield bearing against the external surfaces around the mouth or upper lip. In other applications, the two dentition engagement units are joined by struts, cams, wedges, springs, elastic bands, hooks, screws or combinations thereof to exert an advancement force upon the lower dentition engagement unit and, thereby, to advance the mandible. Examples of such devices in which some form of ramp or wedging element fixed to an upper dentition engagement unit is employed to effect mandibular advance by exerting a force against the lower dentition or a lower dentition engagement unit are those taught by Belfer in U.S. Pat. No. 6,092,523, Palmisano in U.S. Pat. No. 6,604,527, Thornton in U.S. Pat. Nos. 5,427,117 and 5,566,683, Shapiro et al in U.S. Pat. No. 5,117,816 and Hays et al in U.S. Pat. No. 5,092,346. The use of struts of adjustable length to effect mandibular advance are taught by Lowe in U.S. Pat. No. 5,409,017 and Strong in U.S. Pat. Nos. 6,418,933 and 6,526,982. The use of hooks or similar devices to connect a lower dentition engagement unit to an upper dentition engagement unit in a position of mandibular advance is taught by Gaskell in U.S. Pat. No. 6,845,774, Lampert in U.S. Pat. No. 5,823,194 and Halstrom in U.S. Pat. Nos. 5,365,945, 6,041,784, 6,161,542 and 6,729,335. The use of elastic bands to apply a force to effect mandibular advance is taught by Frantz et al in U.S. Pat. Nos. 5,947,724 and 6,109,265. In methods taught by Halstrom in U.S. Pat. No. 5,868,138 and Fenton in U.S. Pat. No. 5,499,633, complementary posts and slots are employed to connect a lower dentition engagement unit to an upper dentition engagement unit in a position of mandibular advance.

To varying degrees, the devices referred to are expensive to purchase, are heavy, are bulky, are uncomfortable in use, are an impediment to speech and breathing, are an impediment to jaw movement, are difficult to clean and sanitise, are difficult to use, and require the services of specialised personnel for individual fitting and adjustment. Specifically, in relation to applications employing forms of ramps or wedging elements fixed to an upper dentition engagement unit to effect mandibular advance by exerting a force against the lower dentition or a lower dentition engagement unit, such applications may effect only a small degree of mandibular advancement. Where a larger degree of mandibular advancement is effected, the rate of displacement of the temporomandibular joint effected in a single jaw closure may cause discomfort in a subject. The grinding sensation as the ramps or wedging elements act upon the lower dentition or lower dentition engagement unit with jaw movement may impart an unpleasant sensation.

The object of the present invention is to provide a device to effect mandibular advancement for the purpose of alleviating snoring and sleep apnoea, the device being inexpensive to purchase, light in weight, compact, easily cleaned and sanitised, which does not require special fitting and adjustment, which allows a user to speak and swallow freely, which is easy and comfortable to use and which permits unrestricted jaw movement, which maintains a constant, comfortable and relatively unobtrusive force to urge the mandible towards an advanced position and to maintain it in an advanced position.

The use of magnets to apply a corrective force to teeth and jaws in orthodontic and orthopaedic procedures is well known. In U.S. Pat. No. 4,871,310, Vardimon teaches the use of magnets elements in a complex apparatus the use of which is directed at correcting sagittal disproportions of the jaws, including overcoming the counterforce of the stretched mandibular muscles. Kurz in U.S. Pat. No. 4,505,672, Dellinger in U.S. Pat. No. 4,396,373, Noble et al in U.S. Pat. No. 3,984,915 and Smiley et al in U.S. Pat. Nos. 4,424,030 and 4,457,707 teach the use of magnets in orthodontic appliances.

According to the present invention, a pair of separate, approximately arcuate dentition engagement units is provided, each having a flat face which abuts a complementary flat face of the other and an opposed dentition engagement face which is adapted to accurately engage, as appropriate, all or part of the maxillary or mandibular dentition. The abutting plane of the flat faces is arranged normal to the sagittal plane. The dentition engagement units are made from polymethylmethacrylate or similar material approved for the purpose. The dentition engagement faces, commonly referred to as dental overlays, preferably engage between 25 percent and 75 percent of exposed tooth depth. They are moulded from dental impressions made in the normal way or created directly by a user by several methods. Dentition engagement faces are created directly by a user by biting into a shaped quantity of suitably softened thermoplastic resin material or settable resin material provided in channels formed on the opposed faces of the dentition engagement units, the material then retaining an impression of the dentition during setting. The thermoplastic material is preferably a thermolabile elastomeric material such as ethylene vinyl acetate. The settable resin is preferably in the form of a stiff paste comprising a suitable resin and filler. The paste is contained in two soft polymer tubes which are injected with a catalysing or curing agent, kneaded to mix the resin and catalyser, pressed in the dentition engagement unit channels and the dental impression taken. Simple locating means are employed to maintain the two dentition engagement units in correct juxtaposition while the dental impressions are made by biting.

The two dentition engagement units are each provided with a pair of laterally located, upwardly-extending flanges positioned in the buccal or lingual region and preferably positioned posterior to the canines. The flanges of the upper dentition engagement unit are located rearmost. With the flat faces of the dentition engagement units abutting, the flanges are positioned adjacent each other and more or less end-to-end with reaction surfaces on the forward edges of the flanges of the upper dentition engagement unit almost abutting complementary reaction surfaces on the rearward edges of the flanges of the lower dentition engagement unit. Suitable small but powerful permanent magnets are embedded longitudinally in the flanges with like poles opposed and almost abutting at the reaction surfaces. In a sleeping and properly relaxed subject, with jaws closed and the flat faces of the dentition engagement units abutting, the magnets generate a sustained force to slowly displace the temporomandibular joint and thereby to advance the mandible and maintain it in the advanced position. The degree of mandibular advancement achieved is sufficient to alleviate the snoring and associated conditions referred to herein.

To provide a supplementary therapeutic effect, provision is optionally made to forwardly displace the uvula by fixing magnetic means to or implanting such means within it and attracting the magnetic means through the use of complementary magnetic means. Such forward displacement of the uvula is acknowledged to similarly alleviate the snoring and associated conditions referred to herein.

The various aspects of the present invention will be more readily understood by reference to the following description of preferred embodiments given in relation to the accompanying drawings in which.

Figure 1:
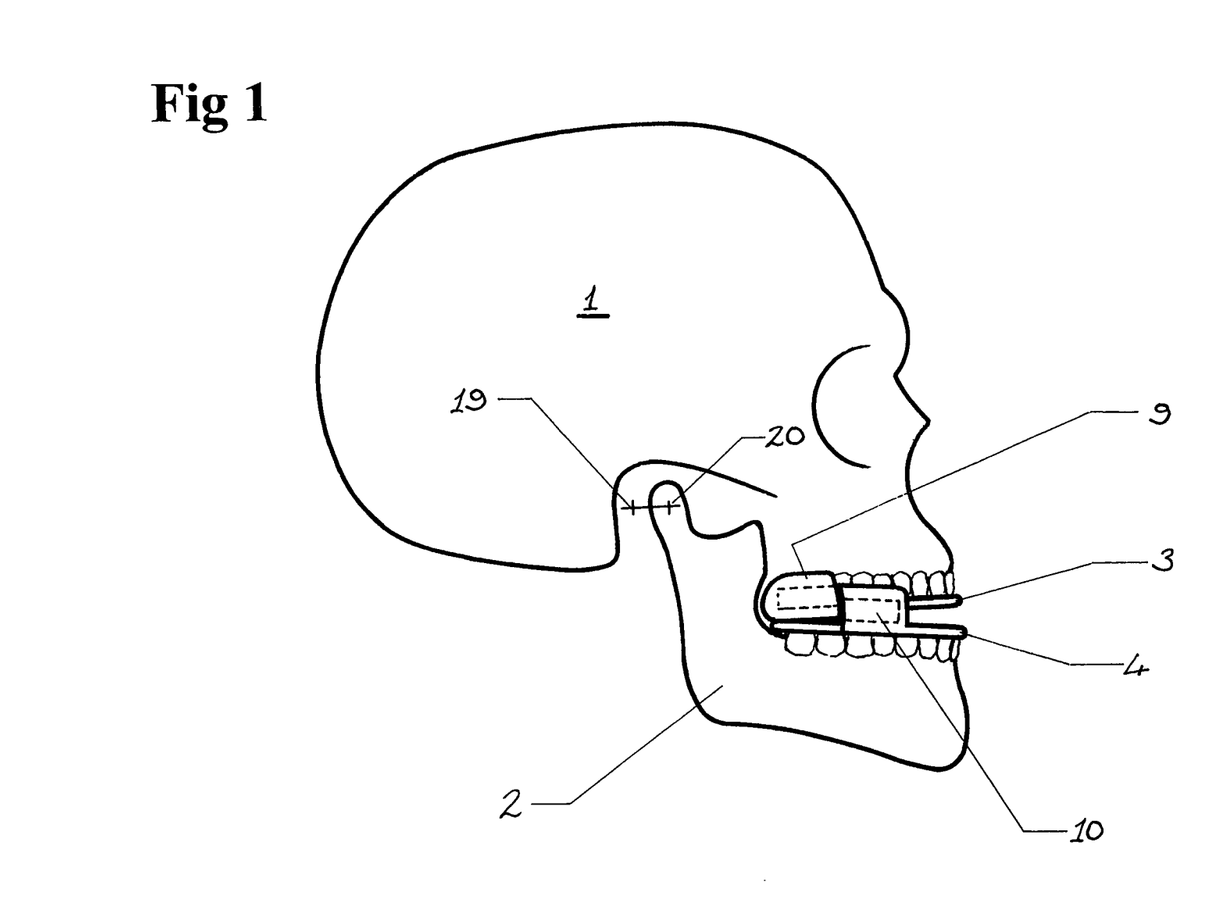
FIG. 1 is a side view of a cranium with mandible in situ and partially open, positioning of the present invention shown.

With reference to FIG. 1, the cranium 1 of a subject is depicted with mandible 2 in situ and partially open. Separate upper and lower, approximately arcuate dentition engagement units 3, 4 are engaged with the subject's teeth. With additional reference to FIGS. 2 and 3, said dentition engagement units have flat faces 5, 6 which are complementary one to the other and which abut when the subject's jaws are closed. Opposed to said flat faces of said dentition engagement units are dentition engagement faces 7, 8 which are moulded to accurately engage, respectively, the subject's maxillary and mandibular dentition. Said dentition engagement faces, commonly referred to as dental overlays, optionally engage all or part of the subject's dentition to between 15 percent and 75 percent of exposed tooth depth. The plane of abutment of said flat faces is arranged normally to the sagittal plane of said cranium. In the preferred embodiment, said dentition engagement units are made from polymethylmethacrylate or similar material approved for the purpose. In the preferred embodiment, said dentition engagement units are moulded by dental technicians in the conventional way employed in the making of dentures and using professionally-made impressions. Such techniques are well known in the art. In an alternative embodiment (not shown), said dentition engagement faces of said dentition engagement units are created directly by users. In a first such method, said dentition engagement faces are created directly by a user by biting into a shaped quantity of suitably softened thermoplastic or settable resin impression receiving material provided in a lipped channel formed on each of the said opposed faces of said dentition engagement units. The impression receiving material then retains an impression of the dentition during setting. Lipping of said channels acts to retain said resin material in place following making of said impressions. In said first method, said thermoplastic resin impression receiving material is preferably a thermolabile elastomeric such as ethylene vinyl acetate. A pair of said dentition engagement unit is placed in water approaching 100° C. until said resin is suitable softened. Said dentition engagement units are then positioned carefully in the subject's mouth, preferably with the use of a mirror, and the subject bites into said softened resin impression receiving material to create an impression, maintaining the jaws closed until said resin impression receiving material has cooled, thereby preserving said impression. The base material of said dentition engagement units is unaffected by said heating. In said second method, said settable resin impression receiving material takes the form of a stiff paste comprising a suitable resin and filler. Said paste is contained in a closed, elongated tube made from a thin, softly flexible, transparent or translucent polymer film material and of a length to suit said lipped channels of said dentition engagement units. In the preferred embodiment said polymer film material is Teflon. Said paste is based upon a settable resin, preferably an acid anhydride-cured epoxy, which has minimum toxicity. Other suitable settable resins are optionally employed. Said polymer tubes are injected with a coloured curing agent provided in small squeezable syringes, kneaded until a specified colour change has occurred, pressed into said lipped channels of said dentition engagement units and dental impressions taken by biting in the manner described. Said impressions must be made within a specified maximum time period before curing of said resin commences. Similarly, the subject's jaws are maintained closed until said resin material has commenced curing and the impression captured, the heat of the mouth helping to accelerate the curing process. In the preferred embodiment, said dentition engagement units are made in a variety of shapes and sizes and the correct one is selected for a particular subject by having the subject bite onto a test piece made from a suitable impressionable material. Each of said upper and lower dentition engagement units is supplied with a forwardly-projecting handle in the form of a flat strip and provision is made to adjust the relative positions of said dentition engagement units to take account of the subject's bite. To preserve said adjustment, said handles are locked together using a simple clamp and maintained so until said impressions have been made in the manner described. Selection and positional adjustment of said dentition engagement units is preferably performed by the supplier. Following making of said impressions, said handles are snapped off at specially provided weakened break points immediately adjacent said dentition engagement units and smoothed using an abrasive stick provided, a manicurist's emery board or the like.

Figure 2:
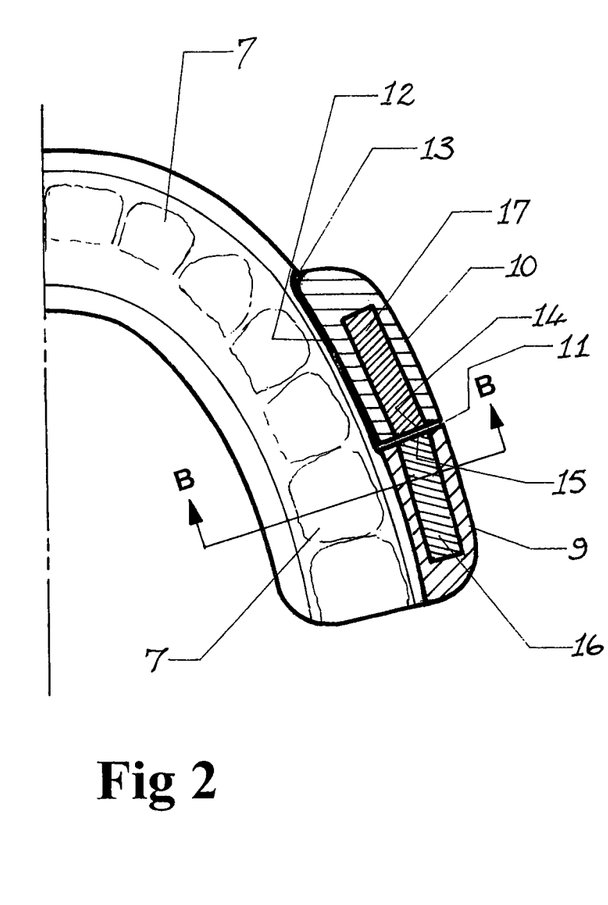
FIG. 2 is a partial cross-sectional view on A-A of the view depicted in FIG. 3.
Figure 3:
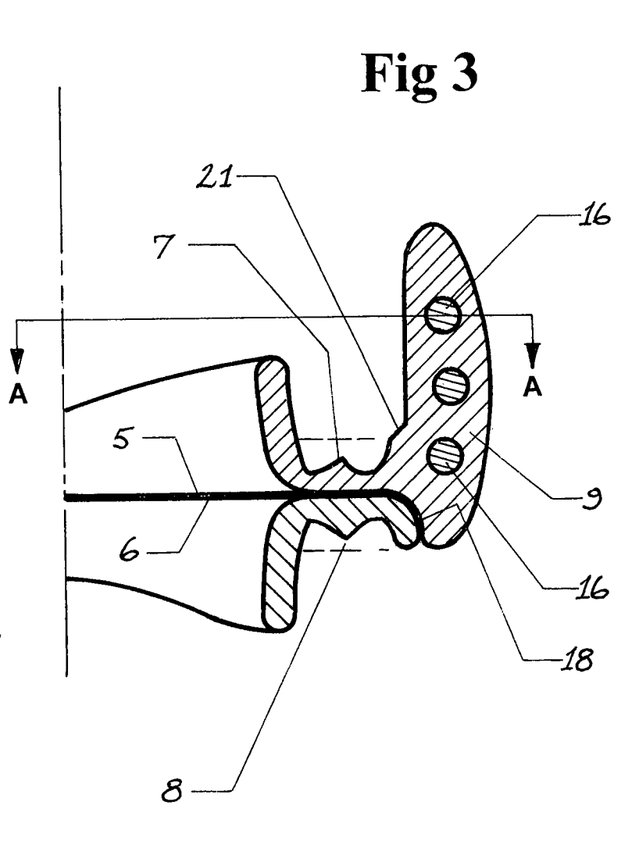
FIG. 3 is a partial cross-sectional view on B-B of the view depicted in FIG. 2.

Each of said upper and lower dentition engagement units is provided with a pair of laterally located, integral extended flanges 9, 10, preferably positioned posterior to the canines. In the preferred embodiment, said flanges are located in the buccal region. Flanges 9 formed on the lateral edges of said upper dentition engagement unit are located rearmost. Flanges 10 formed on the lateral edges of said lower dentition engagement unit overlap the side edges 12 of said upper dentition engagement unit and, with flat faces 5, 6 abutting, occupy a position immediately forward of and more or less end-to-end with flanges 9. For the purposes of user comfort, flanges 9, 10 are provided with suitably rounded edges and, in plan view, are curved to conform to the generality of the adjacent dentition. A suitable working clearance is provided between said side edges 12 of said upper dentition engagement unit and the inner surfaces of flanges 10. A suitable working clearance 11 is provided between the adjacent ends 14, 15 of said flanges, referred to as the reaction surfaces. The side edges 12 of said upper dentition engagement unit are relieved to accommodate flanges 10, shaping of the relief at forward point 13 and overlapping edges 18 being such as to offer no impediment to the forward movement of flanges 10 with mandibular advancement. Shallow steps 21 are provided on the inner surfaces of flanges 9, 10 to ensure clearance from the subject's gum surfaces.

Figure 4:
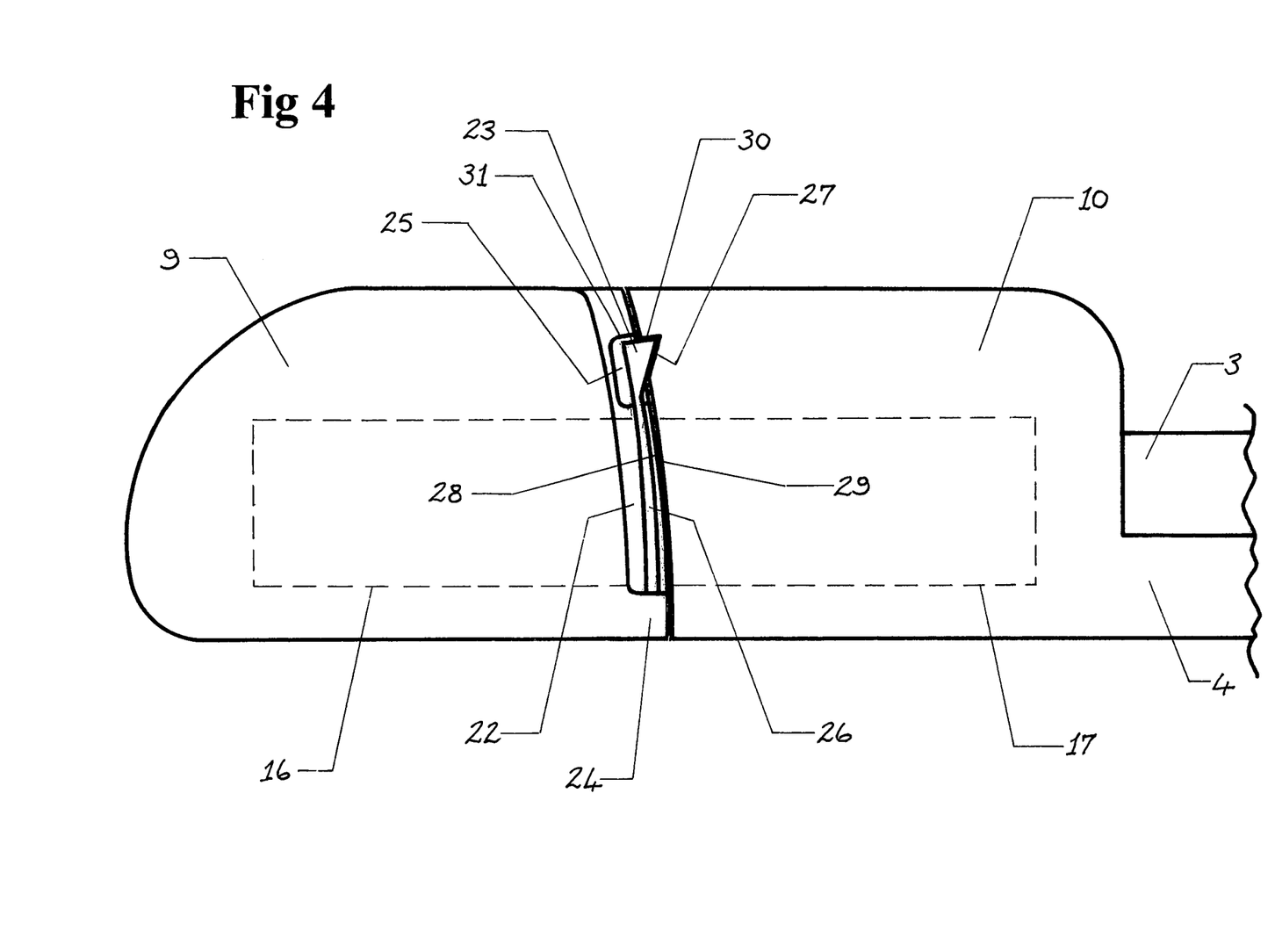
FIG. 4 is a partial side view of a variation of the embodiment depicted in FIG. 1.

One or more suitable small but powerful permanent magnets 16, 17 are embedded longitudinally in each said flange such that, with flat faces 5, 6 in abutment, said magnets are positioned end-to-end. Said magnets are arranged more or less in collinear pairs positioned with like poles opposed and almost abutting at said reaction surfaces. Said magnets optionally extend only partially or substantially along the length of said flanges and are fully encapsulated. In a sleeping and properly relaxed subject, with jaws closed and flat faces 5, 6 of said dentition engagement units abutting, said magnets generate a sustained repulsive force sufficiently powerful to slowly displace the temporomandibular joint from point 19 to point 20 to advance the subject's mandible and thereafter to maintain it in the advanced position. The degree of mandibular advancement required to alleviate snoring and associated conditions referred to herein is normally in the range 5 to 10 millimeters. In the preferred embodiment, said magnets are of the neodymium, rare-earth type which are capable of generating sufficient repulsive effort to effect the required degree of mandibular advancement. As the jaws of a subject are closed from a substantially open position, a resistance to closure will be felt as the like poles of said magnets approach each other. This resistance is, generally speaking, no greater than that felt by the engagement of the ramps or wedging elements of some of the cited prior art upon the lower dentition or lower dentition engagement unit. Said magnets are preferably arranged such that when flat faces 5, 6 are in abutment, said magnets of said lower dentition engagement unit are slightly above said complementary magnets of said upper dentition engagement unit. This has the effect of eliminating all magnetic force directed towards opening the subject's jaws and generating a slight force directed towards closing. With reference to FIG. 4, flanges 9 of upper dentition engagement unit are provided on each side at their outer (forward) edges with rebates 22 extending more or less along the full curved edge 28 of said flanges, but stopping short of the lower edge to create bosses 24. Pawls 23 extend from side to side of each said flange, passing through recesses 25 formed in the forward edges of said flanges. Said pawls are supported on thin, stiffly elastic stalks 26 which are frictionally supported in suitable bores (not shown) formed in said bosses. In the preferred embodiment, said pawls and said stalks are made from a suitable polymer material which lends itself to ready sanitisation. In their free state, said stalks are more or less straight and support said pawls in a position in which they intercept the curved inner edges of flanges 10. With the lower ends of said stalks supported in said bores of said bosses, said stalks are retained in place by their upper edges 30 contacting the upper edges 31 of said recesses. Said pawls and said stalks are readily demounted for cleaning and sanitisation by deflecting said stalks forwardly to disengage said pawls from said recesses and then disengaging the lower ends of said stalks from their said bores. In operation, when the jaws of a user are fully closed, pawls 23 lightly engage detents 27, thereby acting to retain said dentition engagement units in a position with their flat faces 5, 6 in abutment. Accommodated within said rebates and said recesses, said stalks and said pawls produce no discomfort in a user during their displacement. During sleep, said pawls are released from said detents as mandibular advancement occurs in the manner described, said pawls and said detents providing no inhibition to said mandibular advancement. In alternative embodiments (not shown), said stalks and said pawls are optionally incorporated into curved inner edge 29 of flange 10 and both said arrangements are optionally installed in an inverted arrangement.

In an alternative embodiment of the present invention (not shown), said flanges are formed on the lateral edges of said upper and lower dentition engagement units and are orientated downwardly.

In another alternative embodiment (not shown), said flanges are orientated upwardly or downwardly and located in the lingual region.

In another alternative embodiment (not shown), said flanges are made to extend upwardly and downwardly, above and below the plane defining flat faces 5, 6. In this embodiment, the extension above and below said plane optionally ranges from 15 percent of flange height above and 85 percent below, through equidistant, to 85 per, cent of flange height above and 15 percent below.

In another alternative embodiment (not shown), said flanges are made separate and fastenable to said lateral edges of said upper and lower dentition engagement units. In this embodiment, said flanges are made in mating sets having a variety of configurations of height, length and thickness and with various configurations of magnets. Said flanges are fixed to said lateral edges of said dentition engagement units with suitable removable fastenings which, in the preferred embodiment, engage suitable metal inserts embedded in said dentition engagement units.

In another alternative embodiment (not shown), said flanges are made separate and fastenable to said lateral edges of said upper and lower dentition engagement units using complementary, push-in connection means. In this embodiment, said connection means include complementary pins and sockets, dovetail-type connection means and like connection means in which shaped attachment elements are captured in a complementary recess or aperture.

In another alternative embodiment (not shown), where said dentition engagement units are made by dental technicians, said dentition engagement faces are optionally made with thin edge extensions to engage tooth surfaces or with embedded metal clasps of the type incorporated into partial dentures for the purpose of providing more secure attachment to the subject's dentition.

In another alternative embodiment (not shown), where said dentition engagement faces are made directly by a user in the manner described, removable gauges are provided along the edges of said lipped channels to provide a means of correctly locating a subject's teeth prior to the making of impressions in said shaped quantity of thermoplastic or settable resin. Said gauges are poorly adhered to said channel edges and are simply dislodged upon completion of the impression making process.

In other alternative embodiments (not shown), different configurations of said magnets are employed. Alternative magnet configurations include bundles of thin rods, the cross-sectional shape of said bundles being made to provide best filling of the cross-sectional shape of said flanges; multiple rods of larger cross-sectional area which are optionally round, square, hexagonal, triangular or rectangular; flat sheets in parallel or laminated layers; and a single, irregular cross-sectional shape to suit the cross-sectional shape of said flanges.

In operation, the magnetic repulsion employed by the present invention provides a soft and sustained force applied between the upper and lower dentition urging the mandible towards the advanced position, allowing the temporomandibular joint of a subject to be slowly and comfortably displaced during sleep-induced relaxation. The fact that the present invention requires no adjustment in use and that said magnets are fully encapsulated renders cleaning and sanitisation simple. The present, invention is light, comfortable and easy to use.

Figure 5:
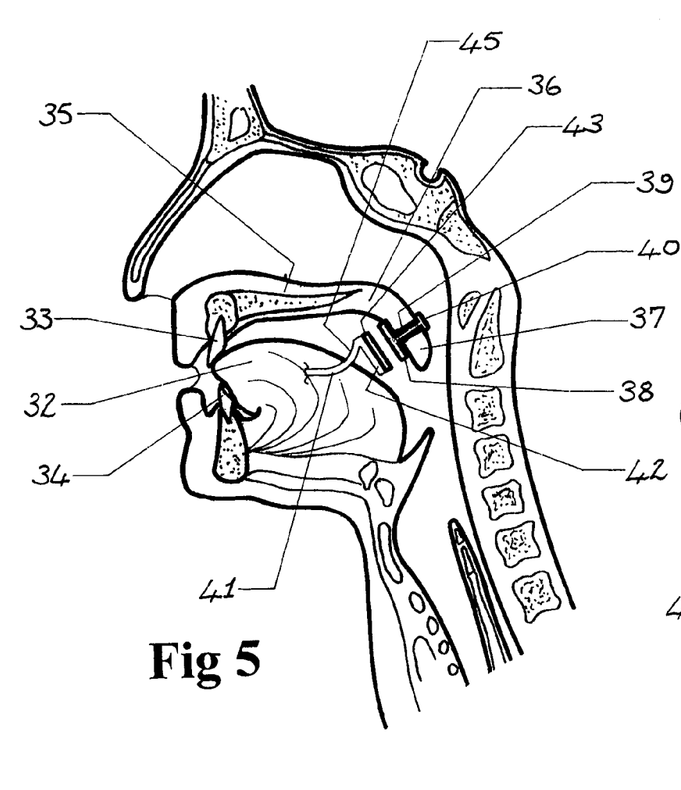
FIG. 5 is a partial cross-sectional view on a sagittal plane of the oropharyngeal region of the human head.

With reference to FIG. 5, a partial cross-sectional view on a sagittal plane is shown of the oropharyngeal region of the human head. The view includes the soft palate 36 suspended from the posterior border of the hard palate 35 and the uvula 37 taking the form of a conical process formed on the lower medial edge of the soft palate. For the purposes of illustration, the tongue 32 is depicted displaced forwardly against the teeth 33, 34 in a position to minimise any tendency towards upper airway blockage. In order to minimise any tendency for the soft palate and uvula to be displaced inwardly and thereby cause upper airway blockage, one or more small, powerful magnets 38 are fixed to the anterior surface of the soft palate and the root of the uvula. In the preferred embodiment, said magnets are fixed to the anterior ends of short stems 39 which pass through suitable holes pierced in the soft palate and uvula, said stems being secured in place by means of suitable retainers 40 fixed to their posterior ends in abutment with the posterior surfaces of said soft palate and uvula. In the preferred embodiment, said retainers are removable and take the form of small, approximately circular plates clipped or screwed to the ends of said stems. Also in the preferred embodiment, said magnets, stems and retainers are, as appropriate, covered with or made from suitable biocompatible materials. In an alternative embodiment (not shown), said magnets are implanted wholly within said soft palate and/or uvula.

Figure 6:
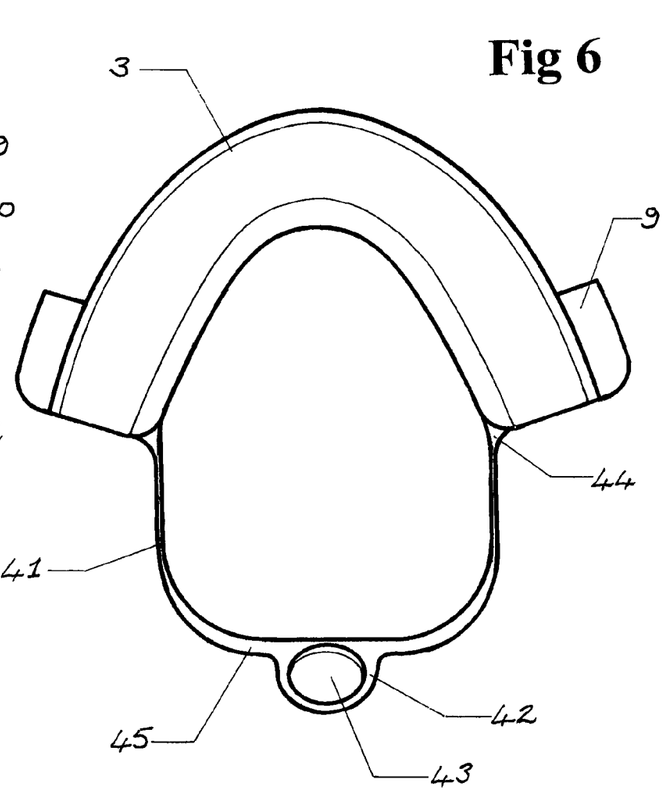
FIG. 6 is a view from above of an alternative embodiment of the upper dentition engagement unit of the present invention.

With additional reference to FIG. 6, the outer ends 44 of inwardly-extending support arms 41 are fixed to the lower, inner ends of upper dentition engagement unit 3. Said support arms pass rearwardly inside the dental arch and along the lateral edges of the tongue in a position in which they offer no impediment to closure of the jaws on said dentition engagement units. Said support arms are joined at their inner ends by arch 45 which passes up and over the posterior part of the tongue. Fixed to the centre of said arch in a position just forward of said soft palate is magnet supporting plate 42 to which; in turn, are fixed one or more small, powerful magnets 43. In the preferred embodiment, magnets 38, 43 are of the neodymium, rare-earth type which are capable of generating sufficient attractive effort to effect and maintain the required degree of forward displacement of said soft palate and uvula. Said magnets are selected such that unlike poles are adjacent when said invention is placed properly in the mouth. In the preferred embodiment, said magnet supporting plate is angled in relation to said arch to support magnets 43 in a position in which they are more or less parallel to magnets 38. In a first alternative embodiment (not shown), magnet supporting plate 42 is fixed to the centre of arch 45 by suitable clamping means, said clamping means being able to be loosened to permit adjustment of the angle of magnets 43 in relation to magnets 38. In a second alternative embodiment (not shown), said magnet supporting plate is made from a suitable soft polymer material in which said magnets are embedded, said soft polymer material providing less discomfort to a user. In a third alternative embodiment (not shown), magnet 38 is embedded in a disk of a suitable soft polymer material. In a fourth alternative embodiment (not shown), magnet supporting plate 42, magnets 43 and magnets 38 are replaced with two complementary disks of a suitable soft polymer material rendered magnetic by the inclusion of magnetic particles, such magnetic polymer materials being well known in the art. Said magnet supporting plate is shaped to accommodate an array of magnets complementary to an array of magnets fixed to or implanted in said soft palate and uvula.

In the preferred embodiment, said support arms are made from a suitable light, stiff material with a cross-sectional shape rectangular or more or less elliptical. The ratio of major to minor axes is in the range 3:1 to 8:1 and the major cross-sectional axis is orientated more or less vertically. To better accommodate the shaping of individual mouths, said support arms are optionally varied in length, varied in spacing, splayed inwardly or outwardly, angled upwardly or downwardly, or joggled upwardly or downwardly at some point along their length. Similarly, said arch is made, to extend higher or lower and is tilted forwardly or rearwardly. In the preferred embodiment, said support arms are made removable, their outer ends 44 being accommodated in complementary channels (not shown) formed in said dentition engagement unit and secured in place with small screws (not shown). In a first alternative embodiment (not shown), said outer ends of said support arms are made tapered and are frictionally captured in complementary sockets provided in said dentition engagement unit. In a second alternative embodiment (not shown), said outer ends of said support arms are simply fixed to said dentition engagement unit. In a third alternative embodiment (not shown), suitable small, powerful magnets are provided at the lower, inner ends of upper dentition engagement unit 3 and complementary small, powerful magnets are provided at the outer ends of inwardly-extending support arms 41, said supporting arms being fixed to said dentition engagement unit by attractive co-operation of the two said pairs of magnets. In the preferred embodiment, said magnets are made annular and pegs extending from a first said pair engage complementary recesses in a second said pair, said embodiment acting to provide improved accuracy and security of attachment of said supporting arms.

In use, said dentition engagement units (depicted as 3, 4 in FIG. 1) are placed in the mouth and, with teeth apart, are pushed into the oral cavity slightly beyond the normal position allowing magnets 38, 43 to engage. Said dentition engagement units are then displaced forwardly into their normal position and retained there by closing of the bite. In forwardly displacing said dentition engagement units in the manner described, said magnets remain engaged, causing said soft palate and uvula to be similarly displaced forwardly and retained in that position. The displaced position of said soft palate and uvula are unaffected by the forward displacement of said mandible and said lower dentition engagement unit in accordance with the operating principles of the present invention.

Figure 7:
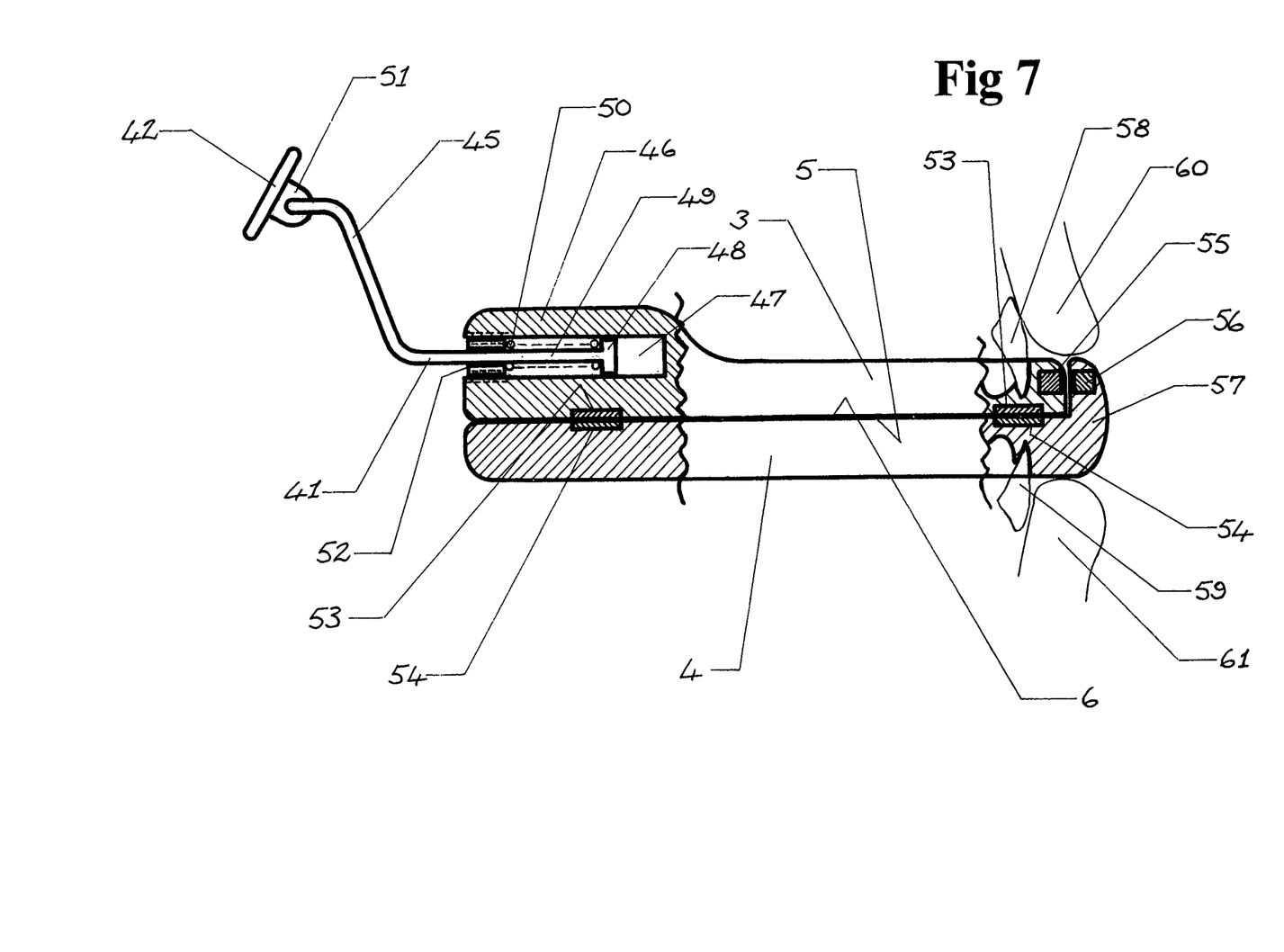
FIG. 7 is a side view of the upper and lower dentition engagement units of the present invention with localised, longitudinal cross-sectionings.

With reference to FIG. 7, in an alternative embodiment, upper and lower dentition engagement units 3, 4 are moulded with impressions of a user's teeth (incisors depicted in ghosted form as 58, 59) and are maintained in the closed bite position by pairs of complementary magnets 53, 54. Said magnets are made weak and do not impede the sliding movement of flat face 5 over flat face 6. Lower dentition engagement unit 4 is made with upwardly extending skirt 57 formed on its forward end, said skirt substantially overlapping the forward end of upper dentition engagement unit 3 with sufficient clearance being allowed between their adjacent surfaces to permit free movement. Suitable strong bar magnets 55, 56 are positioned, respectively, in the forward end of said upper dentition engagement unit and in skirt 57, like poles of said magnets being positioned immediately adjacent each other. The positions of upper and lower lips of a user are depicted in ghosted form, respectively, as 60, 61. I use, when a user is in a fully relaxed sleeping state, the repulsive force of magnet 55 against magnet 56 is sufficient to induce sufficient mandibular advancement to alleviate the symptoms referred to elsewhere herein.

Upper dentition engagement unit 3 is provided on both sides and at the inner end with upper and outward developments 46 which occupy the buccal region of a user's oral cavity. Suitable bores 47 are formed in said developments and are open at their inner ends. Pistons 48 are slidingly accommodated in said bores and are urged in a forward direction by light springs 50. Said springs are retained in said bores by keepers 52, said keepers optionally being installed in said open ends of said bores by suitable threads on their outer surfaces engaging complementary threads in said bores or by suitable lugs on said keepers engaging complementary bayonet-type channels or grooves formed in said bores. The combined, force generated by said springs is just sufficient to positively maintain said uvula clear of the posterior pharyngeal wall. Boss 51 of magnet supporting plate 42 is clamped to and supported on the mid point of arch 45. Said arch is made continuous with parallel support arms 41 which are connected to pistons 48 by parallel piston rods 49. In use, with said dentition engagement units properly installed in a user's mouth and with the magnets of said magnet supporting plate attracting magnets fixed to or implanted in said uvula (as described in relation to FIG. 5), said springs urge said pistons lightly towards a forward position, carrying said arch, said magnet supporting plate, said magnets and said uvula with them, thereby ensuring that said uvula provides no impediment to respiratory airflow. The assembly comprising said pistons, said support arms, said arch, said magnet supporting plate and said magnets is readily removed by disengaging said keepers and withdrawing said pistons from said bores.

In an alternative embodiment (not shown), prior to use, pistons 48 and springs 50 are removed from bores 47, a cylinder of ice or chilled gel material is inserted into each said bore and said pistons and springs re-installed. The presence of said cylinders of ice or gel in said bores maintains piston rods 49 and magnet supporting plates in a rearwardly extended position in which the magnets of said magnet supporting plate readily engage those attached to or implanted in said uvula when said invention is properly installed in the oral cavity. During sleep, said cylinders of ice or gel are progressively warmed by body heat and melt or dissolve, thereby permitting said pistons to be displaced forwardly under the urging of said springs. Suitable small bleed holes (not shown) are provided to permit the escape from said bores of liquid resulting from the melting or dissolving of said ice or gel cylinders. Said forward displacement of said pistons results in a similar displacement of said magnet supporting plate, said magnets and said uvula with them, thereby ensuring that said uvula provides no impediment to respiratory airflow.

In another alternative embodiment (not shown), prior to use, pistons 48 and springs 50 are removed from bores 47, a chilled, stretched cylinder made from a finely foamed, stiff elastomeric material is inserted into each said bore and said pistons and springs re-installed. Between usages, said cylinders are placed in a suitable device (not shown) at room temperature and tension applied to suitably extend their length. Said device is then placed in refrigerated means to cool said cylinders to a temperature in the range −5° C. to −10° C. Immediately prior to use of the present invention, said cylinders are removed from said device, installed in said bores. During sleep, said cylinders are slowly warmed by body heat and resume their unstretched shape, thereby permitting said pistons to be displaced forwardly under the urging of said springs. Said forward displacement of said pistons results in a similar displacement of said magnet supporting plate, said magnets and said uvula with them, thereby ensuring that said uvula provides no impediment to respiratory airflow.

With reference again to FIGS. 5 and 6, in an alternative embodiment (not shown), said support arms and said arch are made from a suitable shape memory polymer material or shape memory metal alloy material having a transition temperature equal to or slightly less than normal body temperature. Between usages of the present invention, said support arms and said arch are preferably detached, clamped in a suitable jig (not shown) to generate a desired distorted shape and cooled in suitable refrigerated means to a temperature substantially below said transition temperature. Said distorted shape is such as to rearwardly displace magnet supporting plate 42 and magnets 43 into a position in which said magnet effectively abuts said magnets fixed to or implanted in said soft palate and/or uvula. Immediately prior to use, said support arms and said arch are reinstalled on said dentition engagement units and said dentition engagement units properly installed in the user's oral cavity such that said magnets of said magnet supporting plate engage said magnets fixed to or implanted in said uvula. As said support arms and said arch are warmed by body heat above the transition temperature of their said material, they slowly resume their undistorted shape, thereby forwardly displacing said magnet supporting plate, said magnets and said uvula to the degree necessary to ensure that said uvula offers no impediment to respiratory airflow.

In an alternative embodiment (not shown), said components of said shape memory material are coated with a suitable thermal insulating material to delay heating to the transition temperature of said shape memory metal alloy material.

In another alternative embodiment (not shown), said components of said shape memory material are made laminated with major and minor laminations such that, at said transition temperature, said major laminate tends to resume the undistorted shapes of said components while said minor laminate simultaneously tends to impede said undistorted shape resumption. Said arrangement acts to slow the rate of resumption of said components of their undistorted shapes.

In another alternative embodiment (not shown), said components of said shape memory material are made thin and encapsulated in a thicker, stiffly elastic polymer material which resists distortion and permits only slow resumption of said undistorted shapes.

Figure 8:
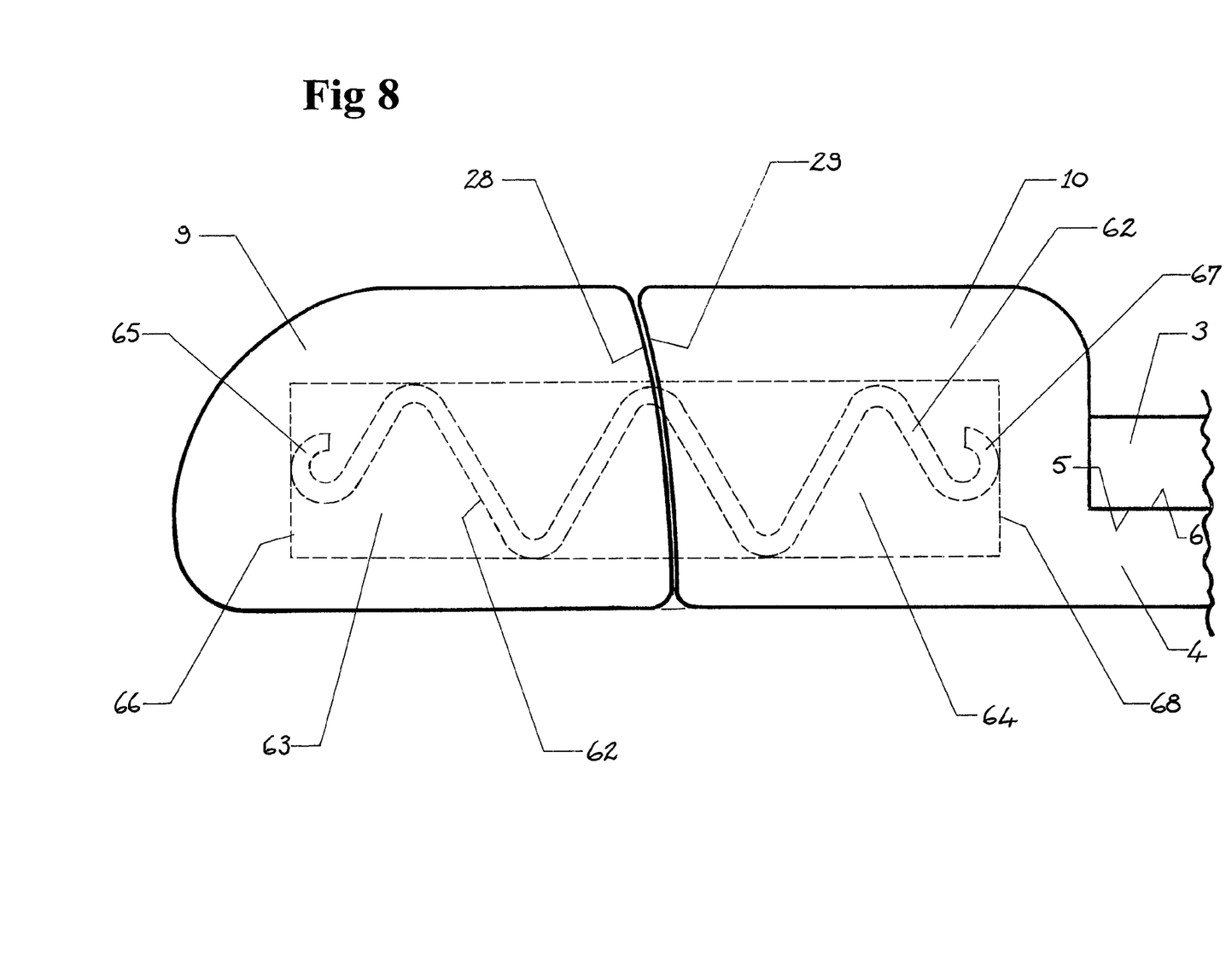
FIG. 8 is a partial side view of a further variation of the embodiment depicted in FIG. 1.

With reference to FIG. 8, said dentition engagement units are made with laterally located, extended flanges 9, 10 situated at either side. Said flanges have formed within them longitudinally extending cavities 63, 64 which, effectively, form single cavities when dentition engagement units 3, 4 are arranged with their flat faces 5, 6 in normal abutment and adjacent curved edges 28, 29 of said flanges are, effectively, in abutment. Accommodated within said cavities are sinusoidally-shaped extension elements 62 made from a suitable shape memory material having a transition temperature equal to or slightly less than normal body temperature. The length of said extension elements and the combined lengths of said cavities are such that the ends 65, 67 of said extension elements in their contracted form abut the end surfaces 66, 68, respectively, of cavities 63, 64. In the preferred embodiment, the ends 65, 67 of said extension elements are rolled or made part-circular to provide bearing surfaces able to smoothly move across said cavity end surfaces as said extension elements change shape. Between usages, said extension elements are placed in a suitable press (not shown) to distort them to a shorter, contracted shape and said press placed in refrigerated means to cool it to substantially below the transition temperature of said shape memory material. Immediately prior to use of the present invention, said press is removed from said refrigerated means, said extension elements are removed from said press and installed in cavities 63, 64, said upper and lower dentition engagement units assembled together in the proper way and the assembled said dentition engagement units placed in the user's oral cavity in the normal way. During sleep, said extension elements are slowly warmed by body heat to the transition temperature of their material and progressively resume their extended, uncontracted shape, the force and degree of displacement of said lower dentition engagement unit so generated being sufficient to effect the degree of mandibular advancement necessary to alleviate the said symptoms.

In the preferred embodiment, said extension elements are made with any suitable cross-sectional shape, including round, oval, square and rectangular. The treatments of said shape memory material detailed in relation to the embodiments depicted in FIGS. 4 and 5 should be taken as applicable to the embodiment depicted in FIG. 8. While only one form of said extension element has been described, it will be understood that said extension elements may be made in any suitable form capable of providing the degree and force of extension required.

Figure 9:
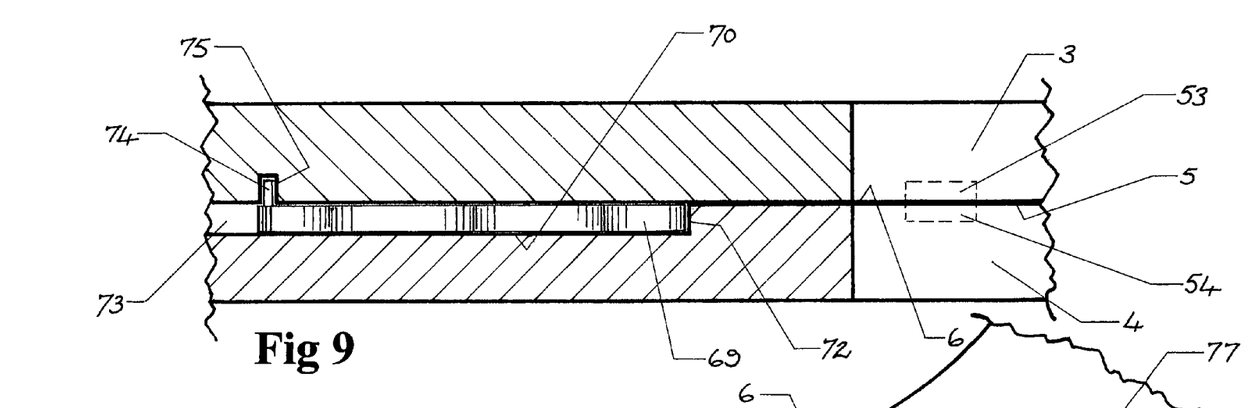
FIG. 9 is a partial longitudinal cross-sectional view on A-A of the embodiment depicted in FIG. 10.
Figure 10:
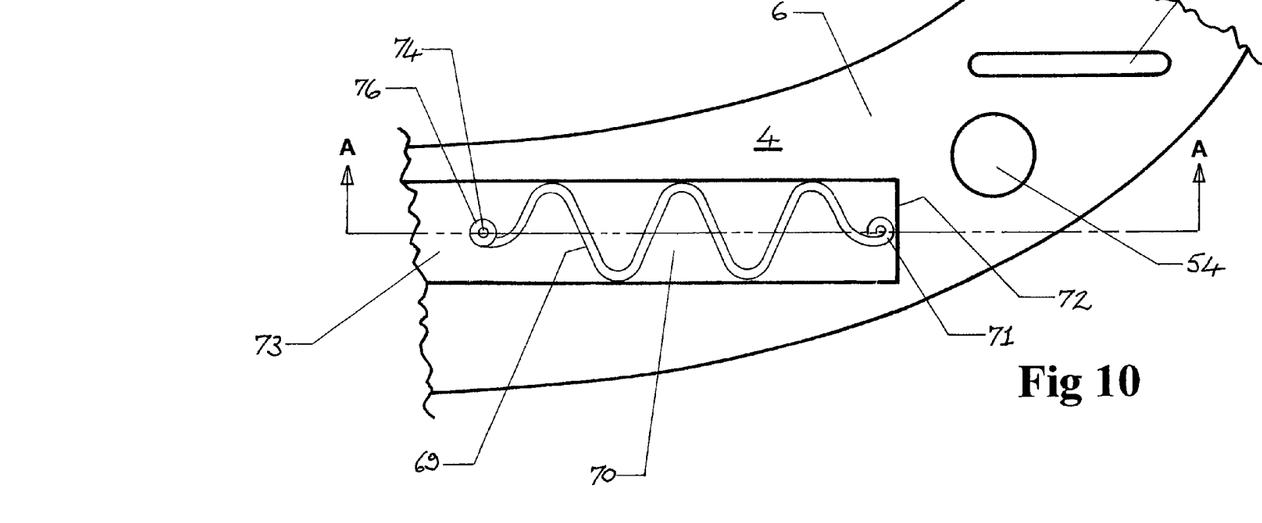
FIG. 10 is a partial view from above of an alternative embodiment of the lower dentition engagement unit.

With reference to FIGS. 9 and 10, the flat faces 5, 6 of upper and lower dentition engagement units 3, 4 are retained in abutment by weak magnets 53, 54 situated at least at two positions throughout their length. Said weak magnets do not materially impede the sliding displacement of one said dentition engagement unit in relation to the other. Two or more shallow, longitudinally arranged; narrow channels are provided in the said flat face of one said dentition engagement unit, said narrow channels being slidingly engaged by complementary buttons (not shown). The provision of said narrow channels and buttons acts to limit the sliding displacement of one said dentition engagement unit in relation to the other to a plane parallel to the sagittal plane. Formed in the upper surface 6 of said lower dentition engagement unit are shallow extension element channels 70 arranged parallel to the sagittal plane. Peg channels 75 arranged normal to the longitudinal plane of said extension element channels and situated immediately above said extension element channels are formed in the flat surface 5 of said upper dentition engagement unit, the length of said peg channels being more or less equal to the width of said extension element channels. Accommodated within said extension element channels are sinusoidally-shaped extension elements 69 made from a suitable shape memory material having a transition temperature equal to or slightly below normal body temperature. The forward or outer ends 71 of said extension elements are rolled or made part-circular to provide bearing surfaces able to smoothly move across the forward or outer end surfaces 72 of said extension element channels as said extension elements change shape. The inner ends of said extension elements are shaped into bosses 76 into which are fixed upwardly projecting pegs 74. When said upper and lower dentition engagement units are assembled together in their normal, un-displaced, relationship and said extension elements are in their contracted form, said pegs engage said peg channels and said forward or outer ends of said extension elements contact said forward or outer end surfaces of said extension element channels. Those parts 73 of said extension element channels positioned inwardly or rearwardly from said peg channels are unoccupied and of a length equal to the maximum displacement distance of said lower dentition engagement unit. Said pegs are able to smoothly move across said peg channels as said extension elements change shape. Between usages, said extension elements are placed in a suitable press (not shown) to distort them to a shorter, contracted shape and said press placed in refrigerated means to cool it to well below the transition temperature of said shape memory material. Immediately prior to use of the present invention, said press is removed from said refrigerated means, said extension elements are removed from said press and installed in extension element channels 70, said upper and lower dentition engagement units are assembled together properly and the assembled said dentition engagement units placed in the user's oral cavity in the normal way. During sleep, said extension elements are slowly warmed by body heat to the transition temperature of their material and progressively resume their extended, uncontracted shape, the force and degree of displacement of said lower dentition engagement unit so generated being sufficient to effect the degree of mandibular advancement necessary to alleviate the said symptoms.

In the preferred embodiment, said extension elements are made with any suitable cross-sectional shape, including round, oval, square and rectangular. The treatments of said shape memory material detailed in relation to the embodiments depicted in FIGS. 4 and 5 should be taken as applicable to the embodiment depicted in FIGS. 9 and 10. While only one form of said extension element has been described, it will be understood that said extension elements may be made in any suitable form capable of providing the degree and force of extension required.

Obviously, where said dentition engagement units are retained with their said flat faces in abutment by said pawls, magnets and the like, they must be removed from the oral cavity for separation.

The invention claimed is:

1. An apparatus for alleviating sleep apnea, comprising:
a maxillary dentition engagement unit or dental overlay shaped to fit a first dental arch of a subject;
a mandibular dentition engagement unit or dental overlay shaped to fit a second dental arch of the subject;
a first flat face disposed on the maxillary dentition engagement unit or dental overlay that is configured to engage a maxillary dentition of the subject;
a second flat face disposed on the mandibular dentition engagement unit or dental overlay that is configured to engage a mandibular dentition of the subject, wherein the second flat face is configured to cooperate in sliding abutment with the first flat face;
a first laterally located pair of flanges formed integrally with or fixed to the maxillary dentition engagement unit or dental overlay;
a second laterally located pair of flanges formed integrally with or fixed to the mandibular dentition engagement unit or dental overlay,
wherein the first laterally located pair of flanges comprises a first flange and a second flange,
wherein the second laterally located pair of flanges comprises a third flange that complements the first flange and a fourth flange that complements the second flange,
wherein one end of the first flange almost abuts one end of the third flange,
wherein one end of the second flange almost abuts one end of the fourth flange,
wherein each of the first, second, third and fourth flanges is elongated, smoothly shaped, and positioned such that an elongated, fully encapsulated magnet having a longitudinal axis is embedded therein, and
wherein the longitudinal axes of the magnets embedded in adjacent flanges are substantially collinearly arranged and with like poles adjacent and almost abutting to provide a magnetically repulsive force, wherein during a state of sleep-induced relaxation of the subject the magnetically repulsive force is sufficient to displace the mandibular dentition engagement unit or dental overlay forwardly in relation to the maxillary dentition engagement unit or dental overlay to forwardly displace a mandible of the subject, open a temporomandibular joint, and reduce a possibility of an airway obstruction;
sprung pawls provided on one of the mandibular or maxillary dentition engagement units or dental overlays; and
engaging detents provided in the other of the mandibular or maxillary dentition engagement units or dental overlays, wherein the sprung pawls and the engaging detents retain the mandibular and maxillary dentition engagement units or dental overlays in a fully engaged position without impeding advancement of the mandibular dentition engagement unit or dental overlay in relation to the maxillary dentition engagement unit or dental overlay.

2. The apparatus of claim 1, wherein the maxillary and mandibular dentition engagement units or dental overlays each further comprise tooth impressions.

3. The apparatus of claim 1, wherein the maxillary and mandibular dentition engagement units or dental overlays each further comprise tooth impressions formed by biting upon tubes filled with a thermosetting impression receiving material inserted into the maxillary and mandibular dentition engagement units.

4. The apparatus of claim 1, wherein the maxillary and mandibular dentition engagement units or dental overlays each further comprise a handle extending therefrom.

5. The apparatus of claim 1, wherein the maxillary and mandibular dentition engagement units or dental overlays each further comprise a handle extending therefrom, and wherein the handle is configured to be removed by snapping off the handle at a breaking point.

6. The apparatus of claim 1, wherein when the maxillary and mandibular dentition engagement units or dental overlays are engaged, a clearance between the corresponding first and third flanges and a clearance between the corresponding second and fourth flanges are sufficient to permit independent movement between the maxillary and mandibular dentition engagement units or dental overlays.

7. The apparatus of claim 1, wherein the first, second, third, and fourth flanges are configured to be located in a buccal region in a mouth of the subject, and are configured to be positioned posterior to canines of the subject.

8. The apparatus of claim 1, wherein the first, second, third, and fourth flanges are configured to be located in a lingual region in a mouth of the subject, and are configured to be positioned posterior to canines of the subject.

9. An apparatus for alleviating sleep apnea, comprising:
a maxillary dentition engagement unit or dental overlay shaped to fit a first dental arch of a subject;
a mandibular dentition engagement unit or dental overlay shaped to fit a second dental arch of the subject;
a first flat face disposed on the maxillary dentition engagement unit or dental overlay that is configured to engage a maxillary dentition of the subject;
a second flat face disposed on the mandibular dentition engagement unit or dental overlay that is configured to engage a mandibular dentition of the subject, wherein the second flat face is configured to cooperate in sliding abutment with the first flat face;
a first laterally located pair of flanges formed integrally with or fixed to the maxillary dentition engagement unit or dental overlay;
a second laterally located pair of flanges formed integrally with or fixed to the mandibular dentition engagement unit or dental overlay,
  wherein the first laterally located pair of flanges comprises a first flange and a second flange,
  wherein the second laterally located pair of flanges comprises a third flange that complements the first flange and a fourth flange that complements the second flange,
  wherein one end of the first flange almost abuts one end of the third flange,
  wherein one end of the second flange almost abuts one end of the fourth flange,
  wherein each of the first, second, third and fourth flanges is elongated, smoothly shaped, and positioned such that an elongated, fully encapsulated magnet having a longitudinal axis is embedded therein, and
  wherein the longitudinal axes of the magnets embedded in adjacent flanges are substantially collinearly arranged and with like poles adjacent and almost abutting to provide a magnetically repulsive force, wherein during a state of sleep-induced relaxation of the subject the magnetically repulsive force is sufficient to displace the mandibular dentition engagement unit or dental overlay forwardly in relation to the maxillary dentition engagement unit or dental overlay to forwardly displace a mandible of the subject, open a temporomandibular joint, and reduce a possibility of an airway obstruction;
sprung pawls provided on the maxillary dentition engagement unit or dental overlay, wherein the sprung pawls are removably supported on thin, stiffly elastic stalks fixed to the maxillary dentition engagement unit or dental overlay; and
engaging detents provided in the mandibular dentition engagement unit or dental overlay, wherein the sprung pawls and the engaging detents retain the mandibular and maxillary dentition engagement units or dental overlays in a fully engaged position without impeding advancement of the mandibular dentition engagement unit or dental overlay in relation to the maxillary dentition engagement unit or dental overlay.

10. The apparatus of claim 9, wherein the maxillary and mandibular dentition engagement units or dental overlays each further comprise tooth impressions.

11. The apparatus of claim 9, wherein the maxillary and mandibular dentition engagement units or dental overlays each further comprise tooth impressions formed by biting upon tubes filled with a thermosetting impression receiving material inserted into the maxillary and mandibular dentition engagement units.

12. The apparatus of claim 9, wherein the maxillary and mandibular dentition engagement units or dental overlays each further comprise a handle extending therefrom.

13. The apparatus of claim 9, wherein the maxillary and mandibular dentition engagement units or dental overlays each further comprise a handle extending therefrom, and wherein the handle is configured to be removed by snapping off the handle at a breaking point.

14. The apparatus of claim 9, wherein when the maxillary and mandibular dentition engagement units or dental overlays are engaged, a clearance between the corresponding first and third flanges and a clearance between the corresponding second and fourth flanges are sufficient to permit independent movement between the maxillary and mandibular dentition engagement units or dental overlays.

15. The apparatus of claim 9, wherein the first, second, third, and fourth flanges are configured to be located in a buccal region in a mouth of the subject.

16. The apparatus of claim 9, wherein the first, second, third, and fourth flanges are configured to be located in a lingual region in a mouth of the subject.

17. An apparatus for alleviating sleep apnea, comprising:
a maxillary dentition engagement unit or dental overlay shaped to fit a first dental arch of a subject;
a mandibular dentition engagement unit or dental overlay shaped to fit a second dental arch of the subject;
a first flat face disposed on the maxillary dentition engagement unit or dental overlay that is configured to engage a maxillary dentition of the subject;
a second flat face disposed on the mandibular dentition engagement unit or dental overlay that is configured to engage a mandibular dentition of the subject, wherein the second flat face is configured to cooperate in sliding abutment with the first flat face;
a first laterally located pair of flanges formed integrally with or fixed to the maxillary dentition engagement unit or dental overlay;
a second laterally located pair of flanges formed integrally with or fixed to the mandibular dentition engagement unit or dental overlay,
  wherein the first laterally located pair of flanges comprises a first flange and a second flange,
  wherein the second laterally located pair of flanges comprises a third flange that complements the first flange and a fourth flange that complements the second flange,
  wherein one end of the first flange almost abuts one end of the third flange,
  wherein one end of the second flange almost abuts one end of the fourth flange,
  wherein each of the first, second, third and fourth flanges is elongated, smoothly shaped, and positioned such that an elongated, fully encapsulated magnet having a longitudinal axis is embedded therein, and
  wherein the longitudinal axes of the magnets embedded in adjacent flanges are substantially collinearly arranged and with like poles adjacent and almost abutting to provide a magnetically repulsive force, wherein during a state of sleep-induced relaxation of the subject the magnetically repulsive force is sufficient to displace the mandibular dentition engagement unit or dental overlay forwardly in relation to the maxillary dentition engagement unit or dental overlay to forwardly displace a mandible of the subject, open a temporomandibular joint, and reduce a possibility of an airway obstruction;

sprung pawls provided on the mandibular dentition engagement unit or dental overlay, wherein the sprung pawls are removably supported on thin, stiffly elastic stalks fixed to the mandibular dentition engagement unit or dental overlay; and engaging detents provided in the maxillary dentition engagement unit or dental overlay, wherein the sprung pawls and the engaging detents retain the mandibular and maxillary dentition engagement units or dental overlays in a fully engaged position without impeding advancement of the mandibular dentition engagement unit or dental overlay in relation to the maxillary dentition engagement unit or dental overlay.

18. The apparatus of claim 17, wherein the maxillary and mandibular dentition engagement units or dental overlays each further comprise tooth impressions.

19. The apparatus of claim 17, wherein the maxillary and mandibular dentition engagement units or dental overlays each further comprise tooth impressions formed by biting upon one or more tubes filled with a thermosetting impression receiving material inserted into the maxillary and mandibular dentition engagement units.

20. The apparatus of claim 17, wherein the maxillary and mandibular dentition engagement units or dental overlays each further comprise a handle extending therefrom.

21. The apparatus of claim 17, wherein the maxillary and mandibular dentition engagement units or dental overlays each further comprise a handle extending therefrom, and wherein the handle is configured to be removed by snapping off the handle at a breaking point.

22. The apparatus of claim 17, wherein when the maxillary and mandibular dentition engagement units or dental overlays are engaged, a clearance between the corresponding first and third flanges and a clearance between the corresponding second and fourth flanges are sufficient to permit independent movement between the maxillary and mandibular dentition engagement units or dental overlays.

23. The apparatus of claim 17, wherein the first, second, third, and fourth flanges are configured to be located in a buccal region in a mouth of the subject.

24. The apparatus of claim 17, wherein the first, second, third, and fourth flanges are configured to be located in a lingual region in a mouth of the subject.

* * * * *